United States Patent [19]

Suga et al.

[11] Patent Number: 4,766,488
[45] Date of Patent: Aug. 23, 1988

[54] FALLING PARTICLE TELEVISING APPARATUS

[75] Inventors: Nagaichi Suga; Shinichi Katayanagi; Yoshio Sasho; Taro Mori, all of Tokyo, Japan

[73] Assignee: Suga Test Instruments Co., Ltd., Tokyo, Japan

[21] Appl. No.: 65,514

[22] Filed: Jun. 23, 1987

[51] Int. Cl.$^4$ .............................................. H04N 7/18
[52] U.S. Cl. ...................................... 358/93; 358/107; 73/865.6
[58] Field of Search ................. 358/105, 107, 101, 93, 358/100; 222/15; 239/14.2; 250/223 R; 73/865.6

[56] References Cited

U.S. PATENT DOCUMENTS

| | | | |
|---|---|---|---|
| 3,187,094 | 6/1965 | Giles | 358/93 |
| 4,514,758 | 4/1985 | Berthel et al. | 358/93 |
| 4,561,018 | 12/1985 | Berthel et al. | 358/100 X |

Primary Examiner—Howard W. Britton
Assistant Examiner—Victor R. Kostak
Attorney, Agent, or Firm—Wenderoth, Lind & Ponack

[57] ABSTRACT

A televising apparatus is provided in a chamber of a snowfall testing system in which various testing conditions may be varied which effect the characteristics of particles of snow generated in the chamber. The televising apparatus has a television camera with an object lens for televising the particles of snow falling in the chamber, and a film feeder for feeding a transparent film, onto which the particles fall, past the object lens. A television camera transfer unit moves the television camera and object lens relative to the transparent film such that the particles falling thereon may be properly and fully televised. Furthermore, a focus regulator is used to move the film feeder and film relative to (toward and away) from the object lens so that the particles falling on the film may be focused. By televising the particles, results of the testing conditions are obtained which can be used to determine the effects of the testing conditions in generating snow within the chamber.

13 Claims, 4 Drawing Sheets

FALLING PARTICLE TELEVISING APPARATUS

BACKGROUND OF THE INVENTION

1. Field of the Invention

This invention relates to a falling particle televising apparatus in a weather-resisting snowfall testing system in which the condition and particle size distribution of the growing crystals of snow produced artificially in a snow generating chamber and a weather-resisting snowfall testing chamber are observed. The results of the observation are used to vary the various artificial snowfall conditions, such as the speed of an ascending air current, temperature, quantity of cloud and seeding rate in the snow generating chamber, and thereby enable various kinds of snow flakes to fall therein.

2. Description of the Prior Art

A conventional falling particle televising apparatus 55, as shown in FIG. 5, is fixedly mounted in a snow generating chamber (inner cylinder) 51.

Such a conventional weather-resisting snowfall testing system consists of a double casing comprised of an outer casing 50, and the snow generating chamber (inner cylinder) 51. The snow is generated in the snow generating chamber (inner cylinder) 51, and the temperature therein is controlled automatically in an indirect manner by cooling the outer circumferential surface of the same chamber 51. Air is introduced into the snow generating chamber (inner cylinder) 51 from the lower portion thereof in an upward direction and is circulated via a duct by a fan 52, and this upwardly-moving air current can be regulated to flow at an arbitrarily chosen flow rate.

When clouds produced by a humidifier 53 are sent into the snow generating chamber (inner cylinder) 51, they move upwardly due to the upward flow of the air introduced therein. When highly-compressed air is then ejected from a special seeding nozzle (seeding means) 54 into the portion of the interior of the snow generating chamber 51 at which the clouds start moving upwardly, cryohydrate, which constitutes the seeds of snow, is produced due to the adiabatic expansion of the air. The clouds act on these seeds and the seeds grow gradually into snow. Consequently, snow consisting of hexapetalous crystals similar to that of natural snow is obtained.

If various conditions, such as the temperature, quantity of the clouds, quantity of the seeds and speed of the upward flow of the air in the snow generating chamber (inner cylinder) 51 are changed in various ways, artificial snowflakes of various sizes and shapes can be obtained.

In order to selectively generate a certain kind of artificial snow, it is necessary to constantly observe the condition of the cryohydrate and snow crystals produced in the snow generating chamber (inner cylinder) 51. A falling particle televising apparatus 55 as shown in FIG. 4 is used as an observation apparatus for this purpose in the snow generating chamber (inner cylinder) 51.

This televising apparatus 55 is provided with an intake 68 in the upper wall of an apparatus body and a film take-up device 67 under the intake 68, a transparent film 57 being provided on the take-up device 67. The falling particles are deposited on the surface of this transparent film 57 as the film 57 is moved horizontally over a predetermined distance at regular time intervals, and the deposited particles are observed through an objective lens of a television camera 56 provided below the film 57.

Referring again to FIG. 5, reference numeral 58 designates a blower for sending the cooling air from a cooler 59 into the interior of the outer casing 50, numeral 60 designates an air compressor, numeral 61 designates a weather-resisting snowfall testing chamber in which a light source 62, a sample 63 and a turntable 64 are disposed, numeral 65 designates a duct, and numeral 66 designates falling particles.

In order to selectively generate a certain kind of snow, for example snow having thin or large flakes, in the snow generating chamber (inner cylinder), it is necessary that various conditions, such as the temperature, quantity of the clouds, quantity of the seeds and speed of the upward flow of the air in the snow generating chamber (inner cylinder) be changed suitably, and the levels of these conditions are determined and set on the basis of the results, which are obtained from the falling particle television apparatus 55, of the observation of the falling particle generating condition.

However, the conventional televising apparatus is simply fixed in the snow generating chamber (inner cylinder). Therefore, the televising apparatus cannot be controlled from the outside. Hence, the observer has to enter the low-temperature environment to regulate the televising apparatus as necessary. Moreover, only the observation of the falling particles at a limited location in the interior of the cylindrical snow generating chamber (inner cylinder) can be done.

Consequently, only a partial and one-phase observation of the condition of generation of falling particles in the snow generating chamber (inner cylinder) can be done. Accordingly, only very limited information for selectively determining the setting levels of the snow generating conditions can be obtained, so that it is difficult to reliably obtain desired kinds of snowflakes.

Under the circumstances, the development of a falling particle televising apparatus capable of observing the condition of the generation of snow at every portion of the interior of the snow generating chamber (inner cylinder) has been in high demand.

The television camera provided in a conventional falling particle televising apparatus in a snow generating chamber (inner cylinder) is a fixed type television camera. In this television camera, the focal length with respect to the surface of the transparent film is regulated in advance, i.e., the distance between an objective lens, which is threaded to an intermediate ring, and the light-receiving surface of the television camera, is regulated by manually loosening the thread-connected object lens.

Therefore, the focal length cannot be varied during the observation of the falling particles, i.e., the focal length cannot be regulated in accordance with the thickness of the snow crystals.

In such a televising apparatus, falling particles having diameters of ten-odd to several hundred microns are magnified 300-600 times and televised, and the image thus obtained is displayed. Accordingly, the thickness of a crystal appears on the display. In order to observe the spaces above and below this crystal the thickness of which is seen on the display, it is necessary that the focusing be done selectively during the televising of falling particles.

In the prior art falling particle televising apparatus, the focal length is set in advance and cannot be regulated later. Therefore, it is difficult to observe the crystals of falling particles thoroughly and accurately.

In order to solve these problems, the development of a televising apparatus capable of free self-adjustment of its focal length to a selected level has been in demand.

Again, in a conventional televising apparatus, the television camera is fixedly mounted, so that the visual field is also fixed. Consequently, the particles deposited on the surface of the film cannot be moved to the center of the visual field. Namely, only a part of the falling particles collected can be observed in practice.

Furthermore, since the take-up means for the transparent film is moved over a predetermined distance at regular time intervals by a motor and a gear, the feed rate of the film cannot be regulated accurately to any selected level. Therefore, the displaying of a crystal as a whole particle deposited on the central portion of the picture frame for the television cannot be done easily, and the crystals of snow cannot be observed satisfactorily.

SUMMARY OF THE INVENTION

The present invention has been developed to solve the above-mentioned problems. It is an object of the present invention to provide a falling particle televising apparatus which is mounted so that it can be moved up and down in the interior of a snow generating chamber and a weather resisting snowfall testing chamber, and which is capable of thoroughly observing the condition and size distribution of the growing crystals of snow being generated artificially in the snow generating chamber. Thus, the results of observation by the televising apparatus can be used to vary the various conditions for producing artificial snow, such as the temperature, quantity of the clouds, quantity of the seeds and speed of the upwardly-moving air current in the snow generating chamber to reliably obtain a desired kind of snow therein.

The present invention employs the following means to solve the problems encountered in the conventional apparatus of the kind discussed above.

As shown in FIG. 1, a television camera 13 is provided on a television camera transfer unit 25 which can be moved in fine increments along both the horizontal X-axis and Y-axis. A transparent film 19 on a film feeder 26 can be moved in fine increments in the horizontal direction. A focus regulator 27 is adapted to move the film feeder 26 in fine increments along the vertical Z-axis to finely regulate the clearance between the surface of the film 19 and an objective lens 12 of the television camera 13. A falling particle televising apparatus 1 consisting of all of these parts is mounted so that the apparatus 1 can be moved up and down in a snow generating chamber 24 and weather-resisting snowfall testing chamber 33 as seen in FIG. 3.

According to the present invention, the falling particle televising apparatus 1 is moved to any selected position by operating a winch means 3 when the snow crystals in the snow generating chamber and weather-resisting snowfall testing chamber 33 are to be observed.

The crystalline particles of snow are deposited from an intake 14 onto the transparent film 19, televised by a television camera 13 and observed on a display (not shown).

The transparent film 19 is moved in fine increments in the horizontal direction by the film feeder 26 and is taken up. Due to the movement of this film 19, the condition of the crystalline particles of snow falling sequentially on the surface thereof is televised continuously by the television camera and is observed.

During this time, an object to be televised can be moved selectively in accordance with the spaces among and the density of the particles by moving the film 19 in fine increments in the horizontal direction by the film feeder 26.

An object to be televised which has a thickness can be focussed properly by moving the film 19 in fine increments in the vertical direction by an operation of the focus regulator 27.

The particles on the surface of the film 19 can be observed thoroughly by moving the television camera 13 in fine increments along the horizontal X-axis or Y-axis by an operation of the television camera transfer unit 25.

The above and other objects as well as advantageous features of the present invention will become apparent from the following description of the preferred embodiment taken in conjunction with the accompanying drawings.

DESCRIPTION OF THE PREFERRED EMBODIMENT

Figure 1:
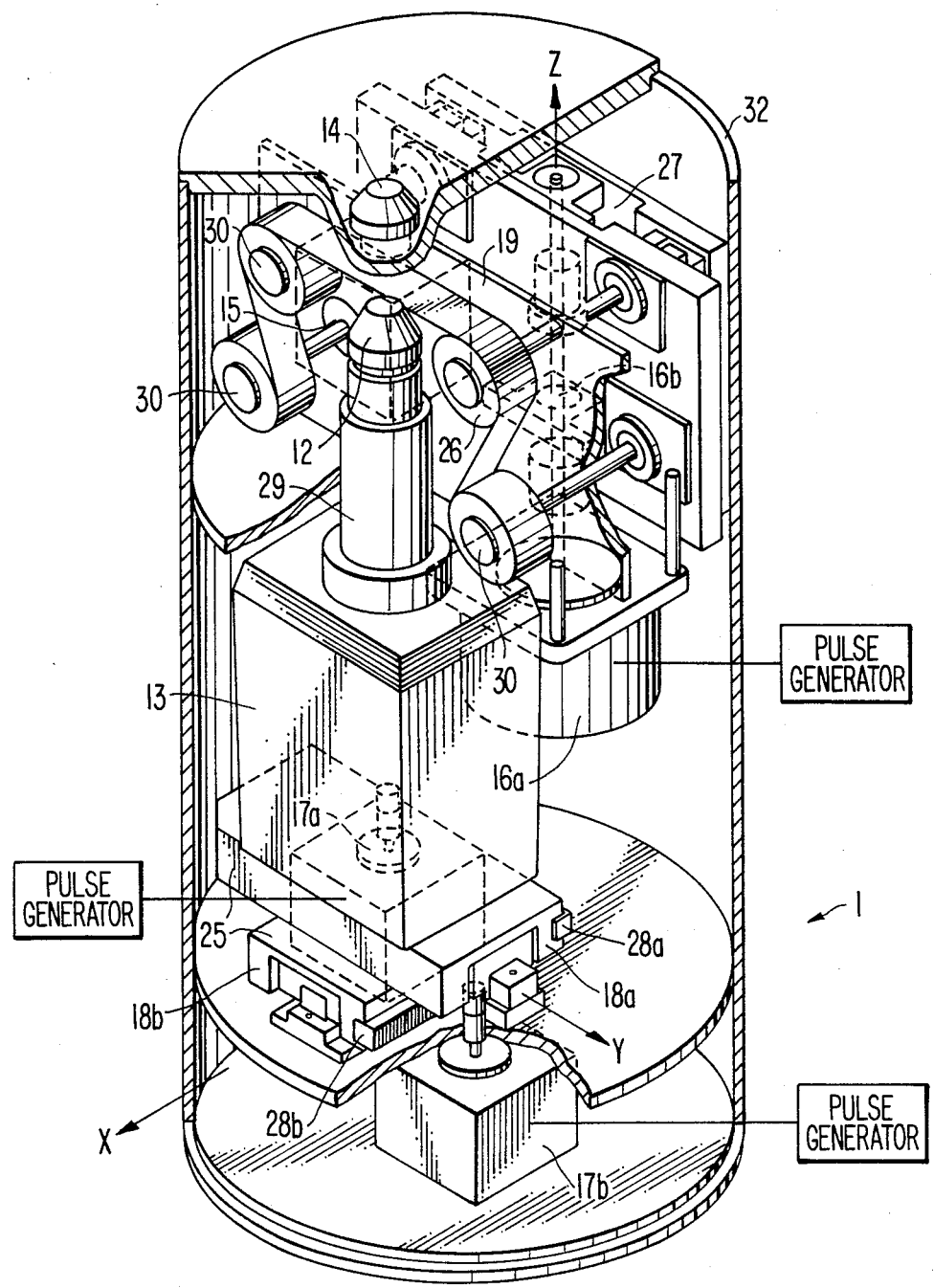
FIG. 1 is a partially cutaway view in perspective of the falling particle televising apparatus according to the present invention.
Figure 2:
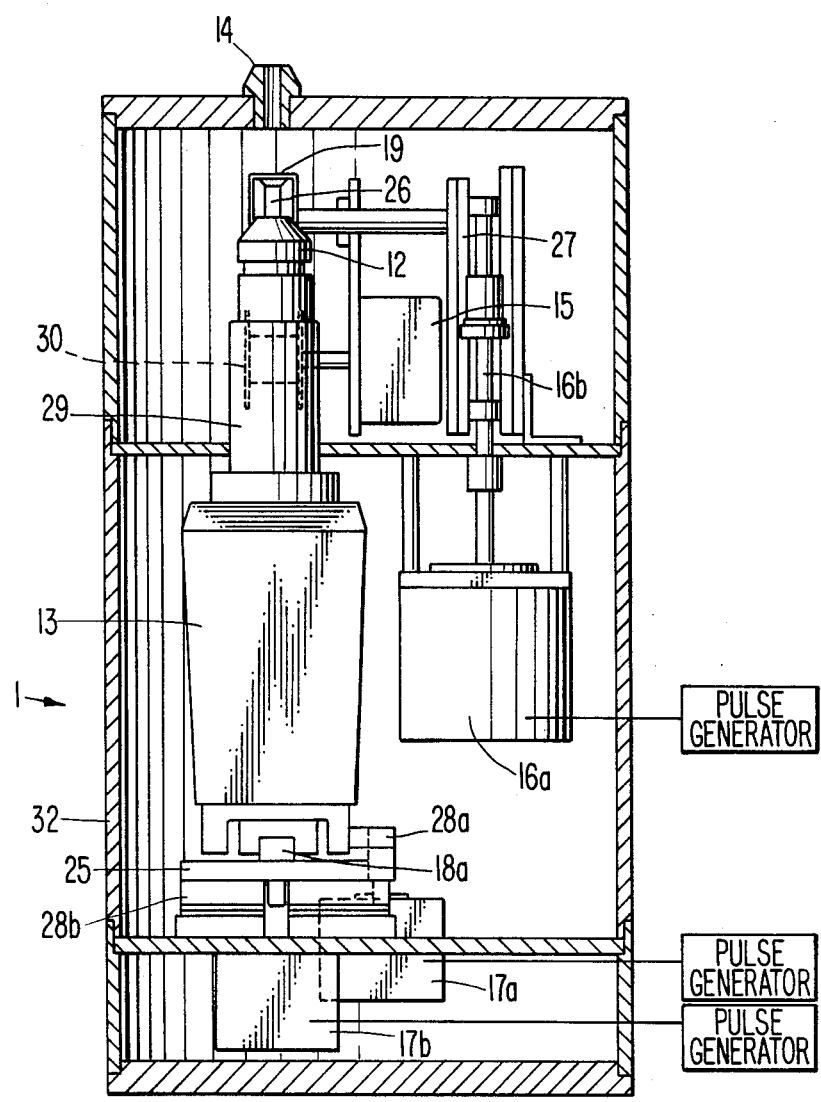
FIG. 2 is a longitudinal section view of the falling particle televising apparatus according to the present invention.

Referring to FIG. 1, the television camera transfer unit 25 consists of two slide blocks 18a, 18b on which racks 28a, 28b are provided, and stepping motors 17a, 17b for driving pinions engaged with the racks 28a, 28b.

These two slide blocks 18a, 18b are stacked so that the directions in which they are moved cross each other at right angles. Known pulse generators, which are provided on the outside of the snow generating chamber 24, are connected to the stepping motors 17a, 17b so that the slide blocks can be moved in fine increments, i.e., several microns per pulse.

The stepping motor 17a is used to move the television camera 13 in fine increments along the horizontal Y-axis, while the stepping motor 17b is used to move the television camera 13 along the horizontal X-axis.

The television camera 13 has an upwardly-directed objective lens 12 and is mounted on the upper slide block 18a so that the television camera 13 can be moved in fine increments along the horizontal X-axis and Y-axis by a remote control operation through the known pulse generator provided on the outside of the snow generating chamber 24.

The film feeder 26 consists of reels 30 provided on both sides of a lens barrel 29 of the television camera 13, and a stepping motor 15 connected to these reels 30. A known pulse generator, which is provided on the outside of the snow generating chamber 24, is connected to the motor 15 so that the film can be moved in fine increments, i.e., several microns per pulse.

The belt-like transparent film 19 for collecting the falling particles is wrapped around the reels 30 in the film feeder 26 so that the film 19 extends above and across from the object lens 12 of the television camera 13 and at right angles to (horizontally with respect to) the optical axis of the television camera 13.

The film 19 can be moved horizontally from one side to the other at a rate of several microns per pulse and taken up by a remote control operation by the reels 30, which are provided on both sides of the lens barrel 29 of the television camera 13, and the stepping motor 15 connected to the reels 30 through the known pulse generator provided on the outside of the snow generating chamber 24.

The focus regulator 27 consists of a stepping motor 16a provided with a ball screw 16b, which is engaged with the film feeder 26. The stepping motor 16a enables the film to be moved in small increments, i.e., several microns per pulse by a remote control operation through the known pulse generator provided on the outside of the snow generating chamber 24.

This focus regulator 27 enables the film feeder 26 to be moved several microns per pulse along the Z-axis (vertical direction) by a remote control operation, and finely regulates the clearance between the surface of the film 19 and the objective lens 12 so that the focusing of the television camera on the particles collected on the surface of the film 19 can be done.

The television camera transfer unit 25, film feeder 16, focus regulator 27 and television camera 13 are housed in a casing 32. The wall of the casing 32 which is opposed to the object lens 12 of the television camera 13 is provided with an intake 14 for particles so that the falling particles, such as the cryohydrate and snow crystals in the snow generating chamber 24 and weather-resisting snowfall testing chamber 33, can be collected sequentially by a remote control operation carried out at the outer side of these chambers, to thereby facilitate the wide-range observation of the particles.

Figure 3:
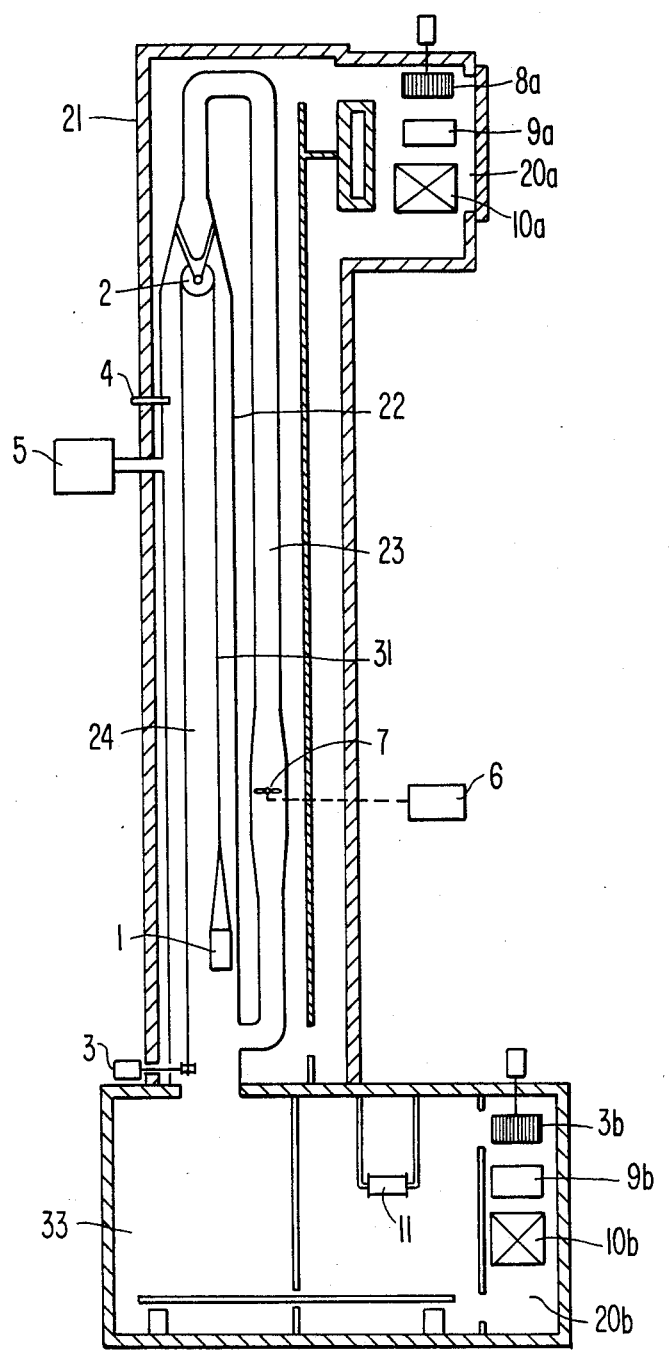
FIG. 3 is a longitudinal section view of a weather-resisting snowfall testing system in which the falling particle televising apparatus according to the present invention is mounted.
Figure 4:
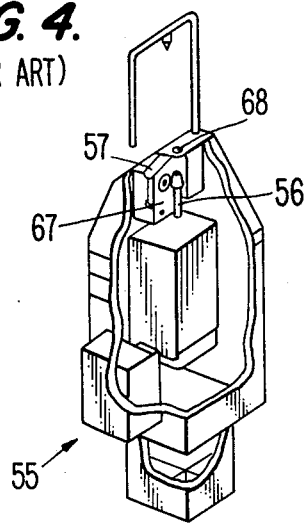
FIG. 4 is a partially cutaway view in perspective of a conventional falling particle televising apparatus.
Figure 5:
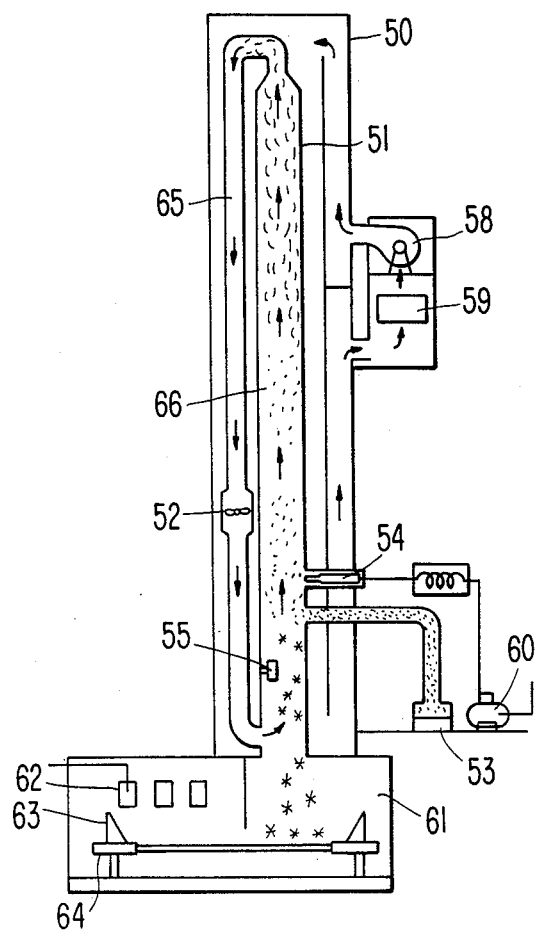
FIG. 5 is a longitudinal section view of a weather-resisting snowfall testing system in which the conventional falling particle televising apparatus is fixedly mounted.

Referring to FIG. 3, a suspender 2 comprising a pulley is provided at a ceiling portion of the snow generating chamber 24, and the falling particle televising apparatus 1 is suspended via a suspending means (wire) 31 and is freely movable in the vertical direction in the snow generating chamber 24 and weather-resisting snowfall testing chamber 33 by a winch means 3.

Referring to FIG. 3, reference numeral 4 designates a seeding means, numeral 5 designates a cloud generating means, numeral 6 designates a means for varying the number of revolutions per unit time of a fan 7 provided in a duct 23, numerals 8a and 8b designate blowers, numerals 9a and 9b designate heaters, numerals 10a and 10b designate coolers, numeral 11 designates a light source, numerals 20a and 20b designate air cooling means, numeral 21 designates an outer casing, and numeral 22 designates an inner cylinder (snow generating chamber).

A process of generating certain types of snowflakes can be observed by setting the focal length of the objective lens 12 of the television camera 13 to a desired level in advance. A concrete process of the growth of the snow can thus be observed.

Due to the above-mentioned advantages of the present invention, the film can be fed in fine increments, by the film feeder, over a required length in accordance with the dimensions of the spaces among and the density of the falling particles, which are deposited on the surface of the film.

The television camera can also be focused to a position in the direction of the thickness of an object as the picture frame of the display is watched during the observation of the object, by moving the film feeder in fine increments with the focus regulator.

The present invention is also capable of displaying every particle, deposited on the film surface, on the picture frame of the television, by moving the object lens with the television camera transfer unit.

As described above, the present invention enables all the falling particles in the snow generating chamber and weather-resisting snowfall testing chamber to be thoroughly observed, and the condition and particle size distribution of the crystals, which are growing into snow, to be determined. Moreover, the condition of snow, which results from the test conditions in the weather-resisting snow fall testing chamber can also be determined, so that a snowfall test can be conducted accurately.

Especially during the observation of a process of the growth of snow, minute particles growing into snow can be visualized moment by moment in succession, so that a concrete process of the growth of particles into snow can be observed.

The various conditions for generating the artificial snowfall in the snow generating chamber, such as the temperature, quantity of clouds, quantity of seeds and speed of the upward flow of the air therein can be regulated on the basis of the results of such an observation. Therefore, a desired kind of artificial snow, such as snow having thin or large flakes, can be obtained.

The present invention is not, of course, limited to the above embodiment. Any modifications that fall within the scope of the appended claims are seen to also fall within the true spirit and scope of the present invention.

What is claimed is:

1. A televising apparatus for televising falling particles in a chamber, said televising apparatus comprising:
    a television camera within the chamber and having an object lens;
    a television camera transfer unit to which said television camera is mounted, said television camera transfer unit being movable in fine increments along both first and second axes for moving said television camera within the chamber along both of said axes, the first and the second axes extending perpendicularly to one another;
    a film feeder for feeding a transparent film, onto which the falling particles fall, in fine increments past said objective lens; and
    a focus regulator for moving said film feeder relative to said object lens in small increments toward and away from the object lens along a third axis which extends perpendicularly to said first and second axes for allowing the particles falling on the transparent film to be focused when televised.

2. A televising apparatus as claimed in claim 1, and further comprising a pulley attached to a top of the chamber, a suspending means reeved around the pulley for suspending the television camera, the televising camera transfer unit, the film feeder and the focus regulator within the chamber, and a winch for reeling the the suspender means in and out to move the television camera, the television camera transfer unit, the film feeder and the focus regulator up and down in the chamber.

3. A televising apparatus as claimed in claim 1, wherein said television camera transfer unit comprises first and second slide blocks slidable along said first and said second axes respectively, a respective rack fixed to each of said slide blocks, a respective pinion engaging each respective said rack, and a respective stepping motor operatively connected to each said respective pinion for rotating the same to drive said first and said second slide blocks along said first and said second axes respectively.

4. A televising apparatus as claimed in claim 3, and further comprising a respective pulse generator for each said respective stepping motor for causing each said stepping motor to slide a respective one of said slide blocks over a distance of several microns for each pulse generated thereby.

5. A televising apparatus as claimed in claim 3, wherein said first slide block is disposed above said second slide block, said television camera is mounted on said first slide block, and said object lens is faced in an upward direction.

6. A televising apparatus as claimed in claim 1, wherein said television camera transfer unit comprises first and second slide blocks, said first slide block is disposed above said second slide block; and said television camera is mounted to said first slide block, and said object lens is faced in an upward direction.

7. A televising apparatus as claimed in claim 1, wherein said television camera has a lens barrel for supporting said object lens; and said film feeder comprises at least one pair of reels, the reels of said at least one pair disposed on opposite sides of said lens barrel from one another, the film passing over said reels, and a stepping motor operatively connected to said reels for rotating said reels in small increments to feed the film passing thereover in small increments.

8. A televising apparatus as claimed in claim 7, wherein said film feeder further comprises a pulse generator for causing the stepping motor of said film feeder to rotate said reels to feed the film in increments equal to several microns for each pulse generated thereby.

9. A televising apparatus as claimed in claim 1, wherein said film feeder comprises a plurality of reels over which the film passes, said reels for positioning a surface of the film onto which the falling particles fall in a plane that is perpendicular to said third axis, the third axis corresponding to an optical axis of the television camera.

10. A televising apparatus as claimed in claim 1, wherein said focus regulator comprises means for moving said film feeder.

11. A televising apparatus as claimed in claim 10, wherein said focus regulator comprises a ball screw to which said film feeder is mounted and a stepping motor operatively connected to said ball screw for rotating said ball screw.

12. A televising apparatus as claimed in claim 11, wherein said focus regulator further comprises a pulse generator for the stepping motor thereof for causing said motor to rotate said ball screw in increments of several microns for each pulse generated thereby.

13. A televising apparatus as claimed in claim 1, and further comprising an outer casing in which the television camera, the television camera transfer unit, the film feeder and the focus regulator are housed for allowing the same to be moved vertically as a unit in the chamber, and said casing having an intake extending therethrough adjacent said object lens of the television camera, said intake for allowing the falling particles in the chamber to pass through said outer casing and onto the film fed by said film feeder past the objective lens.

* * * * *